United States Patent [19]

Quakenbush

[11] Patent Number: 5,099,078
[45] Date of Patent: Mar. 24, 1992

[54] PROCESS FOR PREPARING DINITROTOLUENE

[75] Inventor: Allen B. Quakenbush, Lake Charles, La.

[73] Assignee: Olin Corporation, Cheshire, Conn.

[21] Appl. No.: 632,252

[22] Filed: Dec. 21, 1990

[51] Int. Cl.$^5$ .......................................... C07C 205/06
[52] U.S. Cl. ................................. 568/934; 568/939; 568/940
[58] Field of Search ..................... 568/934, 939, 940

[56] References Cited

U.S. PATENT DOCUMENTS

| 2,362,743 | 2/1943 | Crater | 568/939 |
| 3,928,395 | 12/1975 | Seha et al. | 568/939 |
| 3,957,889 | 5/1976 | Milligan et al. | 568/939 |
| 4,064,147 | 12/1977 | Thelen et al. | 568/939 X |
| 4,367,347 | 1/1983 | Sawicki | 568/934 |
| 4,772,757 | 9/1988 | Lailach | 568/939 |
| 4,804,792 | 2/1989 | Mason et al. | 568/939 |
| 4,918,250 | 4/1990 | Mason et al. | 568/934 |
| 4,935,557 | 6/1990 | Carr | 568/934 |
| 5,001,272 | 3/1991 | Mason | 568/934 |

Primary Examiner—Robert L. Stoll
Assistant Examiner—Chhaya Sayala
Attorney, Agent, or Firm—Dale Lynn Carlson

[57] ABSTRACT

Described herein is a one pot continuous process for preparing dinitrotoluene by reacting toluene with concentrated nitric acid.

6 Claims, No Drawings

PROCESS FOR PREPARING DINITROTOLUENE

FIELD OF THE INVENTION

This invention relates to one pot continuous process for preparing dinitrotoluene by reacting nitric acid with toluene. The process utilizes a nitrate salt to enhance recycle of excess nitric acid and aid in the separation of dinitrotoluene from nitric acid and water.

BACKGROUND OF THE INVENTION

Nitration reactions of aromatic hydrocarbons are generally conducted in mixed acid systems, such as mixed nitric and sulfuric acids. However, these mixed acid systems usually involve reconcentration of the spent sulfuric acid after the nitration reaction. This reconcentration step is time consuming, energy intensive and requires the use of expensive materials of construction. In addition, the use of sulfuric acid tends to result in significant nitrocreosol and cyanide by-product formation which requires expensive waste-water treatment to remove.

In view of these disadvantages associated with mixed nitric/sulfuric acid systems, there have been recent attempts to perform gas phase or liquid phase nitrations in concentrated nitric acid in the absence of sulfuric acid. By way of illustration:

U.S. Pat. No. 2,362,743 discloses a two-step process of the manufacture of dinitrotoluene ("DNT") in the absence of sulfuric acid which comprises (a) nitrating toluene to mononitrotoluene using a nitric acid having a concentration from about 60% to about 75% and a mole ratio of toluene to nitric acid of about 1 to about 3.5 and (b) nitrating the mononitrotoluene to dinitrotoluene using nitric acid having a concentration of from about 90% to about 100%, and a mole ratio of mononitrotoluene to nitric acid of about 1 to about 3. Although the process of this patent is advantageously conducted in the absence of sulfuric acid, it was found that in step (b), a very high percentage of the nitrated product (up to 25%) based upon the amount of toluene reactant employed does not phase separate from the nitric acid medium. The patent teaches vacuum distillation of the product mixture to isolate the desired dinitrotoluene, which is an expensive and highly energy intensive process step.

U.S. Pat. No. 3,928,395 describes a process for nitrating unsubstituted or substituted benzene at a reaction temperature of −40° C. to 80° C. using 90% to 100% nitric acid in the optional and preferred presence of a dipolar aprotic solvent, wherein the reaction is halted by means of a dipolar aprotic solvent.

U.S. Pat. No. 3,957,889 describes an improved process for nitrating toluene or ortho-xylene with nitric acid, the improvement being enhancing the rate of the nitration reaction by carrying it out in the presence of at least an effective amount of anhydrous calcium sulfate or soluble anhydrite.

U.S. Pat. No. 4,064,147 describes the preparation of aromatic mononitro compounds (such as mononitrobenzene) by a liquid phase reaction with nitric acid having an acid concentration of between 70 percent and 100 percent by weight using a reaction temperature of between 0° C. and 80° C. When employing a relatively reactive compound such as benzene or toluene as a starting material, this patent teaches that a nitric acid concentration of between 70 and 90 percent by weight is preferred. The process of this patent requires a ratio of nitric acid plus water to organic components of not below 3 when using 70% nitric acid, and not below 8 when using 100% nitric acid. However, it has now been found that such a high acid ratio using 100% nitric acid tends to favor dinitro-compound production, not desired by the process of the patent.

U.S. Pat. No. 4,804,792 describes the nitration of benzene and toluene by contacting these with concentrated nitric acid in the presence of a molten nitrate salt. The patent states that the molten salt serves as a temperature regulator for the reaction and as an isothermal medium for the reactants. A preferred method of contacting the reactants in the presence of the molten salt is stated to be by bubbling the reactants into a bath of the molten salt by means of a carrier gas such as nitrogen. The vapor phase reaction is stated to be carried out at a temperature of between 150° C. and 250° C.

U.S. Pat. No. 4,918,250 describes a process for nitrating toluene to dinitrotoluene (DNT) and phase separation of the product using an inorganic salt as a phase separation agent. In this patent, DNT is produced in a two-step liquid phase nitration reaction between nitric acid and toluene in the absence of sulfuric acid and solvent. In the process of the patent, the inorganic salt is incorporated into the mixture of DNT and unreacted nitric acid in an amount sufficient to cause phase separation of the mixture in order to facilitate isolation of the DNT from the unreacted nitric acid in the product mixture (column 2, lines 27 to 33).

Since dinitrotoluene is useful as an intermediate in producing toluene diisocyanate, new processes for the selective manufacture of this intermediate would be highly desirable to the polyisocyanate manufacturing community.

DESCRIPTION OF THE INVENTION

The instant process produces dinitrotoluene from toluene and concentrated nitric acid in a one pot continuous process. The homogenous reaction of this invention simplifies operating and safety requirements as compared to a two step process which first produces mononitrotoluene and then reacts the mononitrotoluene in a second pot with acid to produce the dinitrotoluene.

Specifically, this invention is directed to a continuous one pot process for the production of dinitrotoluene comprising the following steps:

(a) reacting toluene with concentrated nitric acid to produce a product mixture containing dinitrotoluene, unreacted nitric acid and water;

(b) then mixing the product mixture from step (a) with a substantially dehydrated molten nitrate salt;

(c) then adding additional nitric acid to the mixture of step (b);

(d) then separating nitric acid from the mixture from step (c) in the form of a vapor to form a two phase liquid mixture;

(e) then separating the dinitrotoluene phase from the liquid hydrated salt phase;

(f) then treating the acid vapor from step (d) and the hydrated salt-liquid phase of step (e) to separate and concentrate nitric acid for recycle to step (a);

(g) dehydrating the nitrate salt solution; and (h) recycling the dehydrated nitrate salt to step (b).

The dinitrotoluene may then be further purified to the desired specifications. The one pot continuous process of this invention provides an efficient method for preparing dinitrotoluene.

In the process of this invention, toluene is reacted with concentrated nitric acid (an acid concentration of between 95 and 100 weight percent, preferably at least 98 weight percent) at a temperature of from about 25° C. to about 90° C., preferably from about 40° C. to about 70° C. to produce an effluent mixture of dinitrotoluene, water and unreacted nitric acid.

The reaction is homogenous and the reactor is generally agitated to enhance the reaction rate. Thus, a stirred tank reactor is preferred.

The molar ratio of toluene to concentrated nitric acid employed in the reaction is generally between about 9:1 and 6:1. The reaction is generally conducted at atmospheric pressure, although a higher pressure can be employed, if desired. The reaction time is typically less than about 4 hours, preferably less than about 40 minutes.

The effluent mixture of dinitrotoluene, water and unreacted nitric acid is then mixed with a substantially dehydrated molten nitrate salt. The nitrate salts which may be used in the process of this invention include a wide variety of nitrate salts which may be in various hydrated states. The preferred salts have a melting point of about or below 70° C.

Preferred molten nitrate salts include the calcium nitrate hydrates such as calcium nitrate tetrahydrate; the lithium nitrate hydrates such as lithium nitrate hydrate; the manganese nitrate hydrates such as manganese nitrate tetrahydrate; the magnesium nitrate hydrates such as magnesium nitrate trihydrate, and magnesium nitrate hexahydrate; the zinc nitrate hydrates such as zinc hexahydrate, and mixtures of one or more of the nitrate salts. A particularly effective molten nitrate salt is a combination of a zinc nitrate hydrate and a magnesium nitrate hydrate, i.e., zinc nitrate trihydrate and magnesium nitrate trihydrate. Minor amounts of other molten salts may be included such as alkali sulfates as long as the melting point of the molten salt used in the process does not exceed about 70° C.

The molten salts are used in amounts of from about 0.5 to about 25.0 parts, preferably from about 1.0 to about 15.0 parts based on the amount 1.0 part, by molar basis of toluene.

After mixing the reactor effluent and nitrate salt, the reaction may be stopped since excess nitrate in solution inhibits further nitration. Fresh nitric acid is then added to the reactor effluent and nitrate salt mixture to make up the acid consumed in the reaction. The fresh acid may be concentrated or diluted.

The mixture is then fed to a flash drum to separate most of the nitric acid as a vapor. The heat required to flash the acid is provided by the hot dehydrated molten nitrate salt. Any other heat requirements may be provided by, for example, a steam heater on the flash drum.

The remaining mixture of nitrate salt, water, nitric acid and dinitrotoluene is a two phase mixture. The two phase mixture may be separated by mechanical means such as a settling tank or centifuge. One phase is crude dinitrotoluene containing trace nitric acid and the other phase is nitrate salt with water and trace nitric acid. After phase separation, the crude dinitrotoluene may be further purified to the desired product specifications.

The hydrated salt stream and the nitric acid vapor are fed to a fractionation column. The salt raises the volatility of the nitric acid allowing concentrated nitric acid to be removed overhead as a vapor or liquid. Using the nitrate salt allows for the efficient removal of the product from the acid solution and provides an energy efficient method to separate acid from the water formed during the reaction. The concentrated nitric acid may then be recycled to the nitration reactor(s). The concentrated acid column can be operated at atmospheric or reduced pressures.

After removal of the acid, the remaining salt and water of the fractionation column bottoms is further treated. This stream contains a small amount (less than 1%) of nitric acid. The solution is heated in a flash drum to dehydrate the nitrate salt. The water removed from the salt contains a small amount of nitric acid. The weak solution is fed to a fractionation column to concentrate the acid. The resulting dilute acid stream may be combined with the fresh acid stream.

While the invention has been described above with reference to specific embodiments thereof, it is apparent that many changes, modifications, and variations can be made without departing from the inventive concept disclosed herein. Accordingly, it is intended to embrace all such changes, modifications, and variations that falls within the spirit and broad scope of the appended claims. All patents cited herein are incorporated by reference in their entirety.

What is claimed is:

1. A continuous one pot process for the production of dinitrotoluene comprising the following steps:
    (a) reacting toluene with concentrated nitric acid to produce a product mixture containing dinitrotoluene, water and unreacted nitric acid;
    (b) then mixing the product mixture form step (a) with a substantially dehydrated molten nitrate salt to facilitate the separation of said dinitrotoluene from said water and said unreacted nitric acid in said product mixture;
    (c) then adding additional nitric acid to the mixture of step (b) in order to make up the acid consumed in step (a);
    (d) then separating a portion of the nitric acid as a vapor from the mixture of step (c) to provide a remaining mixture having two phases wherein a first phase consists essentially of crude dinitrotoluene containing trace amounts of nitric acid and a second phase consists essentially of hydrated nitrate salt with water and trace amounts of nitric acid;
    (e) then separating the first phase from the remaining mixture of step (d) to provide a hydrated salt stream;
    (f) then treating the vapor from step (d) with the hydrated salt stream of step (e) to separate and concentrate nitric acid for recycle to step (a);
    (g) dehydrating the hydrated nitrate salt from said hydrated salt stream;
    (h) recycling the dehydrated nitrate salt recovered from step (g) to step (b).

2. A process as defined in claim 1 wherein the molten salt of step (b) is selected from the group consisting of one or more of sodium nitrate, potassium nitrate, calcium nitrate hydrates, lithium nitrate hydrates, manganese nitrate hydrates, magnesium nitrate hydrates, and zinc nitrate hydrates.

3. A process as defined in claim 2 wherein the molten salt is a combination of zinc nitrate hydrate and magnesium nitrate hydrate.

4. A process as defined in claim 1 wherein step (a) is conducted at a temperature of from about 25° C. to about 90° C.

5. A process as defined in claim 1 wherein the molar ratio of dilute nitric acid to toluene in step (a) is between about 9:1 and 6:1.

6. A process as defined in claim 1 wherein the molten salts in step (b) are used in amounts of about 0.5 to about 25.0 parts based on the amount 1.0 part by molar basis of toluene.

* * * * *